United States Patent
Wang et al.

(12)

(10) Patent No.: US 6,509,320 B1
(45) Date of Patent: Jan. 21, 2003

(54) PURINE L-NUCLEOSIDES, ANALOGS AND USES THEREOF

(75) Inventors: Guangyi Wang; Robert Tam; Devron Averett, all of Irvine, CA (US)

(73) Assignee: ICN Pharmaceuticals, Inc.

(*) Notice: Subject to any disclaimer, the term of this patent is extended or adjusted under 35 U.S.C. 154(b) by 0 days.

(21) Appl. No.: 09/594,271

(22) Filed: Jun. 15, 2000

Related U.S. Application Data

(62) Division of application No. 09/291,907, filed on Apr. 14, 1999
(60) Provisional application No. 60/028,586, filed on Oct. 16, 1996, provisional application No. 60/043,974, filed on Apr. 23, 1997, and provisional application No. 60/055,487, filed on Aug. 12, 1997.

(51) Int. Cl.$^7$ .................. A61K 31/70; C07H 19/02; C07H 19/14
(52) U.S. Cl. .................. 514/43; 536/27.21
(58) Field of Search .................. 514/43, 45; 536/27.21, 536/27.81

(56) References Cited

U.S. PATENT DOCUMENTS

| | | | | |
|---|---|---|---|---|
| 5,248,776 A | * | 9/1993 | Chu et al. | 544/310 |
| 5,473,063 A | * | 12/1995 | Classon et al. | 536/122 |
| 5,559,101 A | * | 9/1996 | Weis et al. | 514/45 |
| 5,561,120 A | * | 10/1996 | Lin et al. | 514/49 |
| 5,565,438 A | * | 10/1996 | Chu et al. | 514/50 |
| 5,567,688 A | * | 10/1996 | Chu et al. | 514/46 |
| 5,567,689 A | * | 10/1996 | Sommadossi et al. | 514/50 |
| 5,587,362 A | * | 12/1996 | Chu et al. | 514/46 |
| 5,599,796 A | * | 2/1997 | Schinazi et al. | 514/44 |
| 5,627,160 A | * | 5/1997 | Lin et al. | 514/49 |
| 5,631,239 A | * | 5/1997 | Lin et al. | 514/49 |

FOREIGN PATENT DOCUMENTS

| | | | |
|---|---|---|---|
| EP | 0343945 | * | 11/1989 |
| WO | 8905649 | * | 6/1989 |
| WO | 8905817 | * | 6/1989 |

* cited by examiner

*Primary Examiner*—James O. Wilson
*Assistant Examiner*—Eric Crane
(74) *Attorney, Agent, or Firm*—Fish & Associates, LLP; Robert D. Fish; Sandra Thompson

(57) ABSTRACT

Novel purine L-nucleoside compounds are disclosed, in which both the purine rings and the sugar are either modified, functionalized or both. The novel compounds or pharmaceutically acceptable esters or salts thereof may be used in pharmaceutical compositions, and such compositions may be used to treat an infection, an infestation, a neoplasm, or an autoimmune disease. The novel compounds may also be used to modulate aspects of the immune system, including modulation of Th1 and Th2.

3 Claims, 3 Drawing Sheets

PURINE L-NUCLEOSIDES, ANALOGS AND USES THEREOF

This is a division of U.S. application Ser. No. 09/291,907, filed Apr. 14, 1999, which claims priority to provisional application ser. No. 60/028,586, filed Oct. 16, 1996, provisional application ser. No. 60/043,974, filed Apr. 23, 1997, and provisional application ser. No. 60/055,487, filed Aug. 12, 1997.

FIELD OF THE INVENTION

The present invention relates to the field of L-nucleosides.

BACKGROUND OF THE INVENTION

The last few decades have seen significant efforts expended in exploring possible uses of D-nucleoside analogs as antiviral agents. Some of this work has borne fruit, and a number of nucleoside analogs are currently being marketed as antiviral drugs, including the HIV reverse transcriptase inhibitors (AZT, ddI, ddC, d4T, and 3TC).

A variety of purine D-nucleoside analogs have also been explored in search of immuno-modulators. Guanosine analogs having substituents at the 7- and/or 8-positions, for example, have been shown to stimulate the immune system (for a review, see: Weigle, W. O. CRC *Crit. Rev. Immunol.* 1987, 7, 285; Lin et al. *J. Med. Chem.* 1985, 28, 1194–1198; Reitz, et al. *J. Med. Chem.* 1994, 37, 3561–3578, Michael et al. *J. Med. Chem.* 1993, 36, 3431–3436). Certain 3-β-D-ribofuranosylthiazolo[4,5-d]pyrimidines have also demonstrated significant immunoactivity, including murine spleen cell proliferation and in vivo activity against Semliki Forest virus (Nagahara, et al. *J. Med. Chem.* 1990, 33, 407–415; Robins et al. U.S. Pat. No. 5,041,426). In other research, 7-Deazaguanosine and analogs have been shown to exhibit antiviral activity in mice against a variety of RNA viruses, even though the compound lacks antiviral properties in cell culture. 3-Deazaguanine nucleosides and nucleotides have also demonstrated significant broad spectrum antiviral activity against certain DNA and RNA viruses (Revankar et al. *J. Med. Chem.* 1984, 27, 1389–1396). Certain 7- and 9-deazaguanine C-nucleosides exhibit the ability to protect mice against a lethal challenge of Semliki Forest virus (Girgis et al. *J. Med. Chem.* 1990, 33, 2750–2755). Certain 6-sulfenamide and 6-sulfinamide purine nucleosides have demonstrated significant antitumor activity (Robins et al. U.S. Pat. No. 4,328,336). Certain pyrimido[5,4-D]pyrimidine nucleosides were effective in treatment against L1210 in BDF1 mice (Robins et al. U.S. Pat. No. 5,041,542), and there, the antiviral and antitumor activities of the above mentioned nucleosides were suggested to be the results of the their role as immunomodulators (Bonnet et al. *J med. Chem.* 1993, 36, 635–653).

One possible target of immunomodulation involves stimulation or suppression of Th1 and Th2 lymphokines. Type I (Th1) cells produce interleukin 2 (IL-2), tumor necrosis factor (TNF∀) and interferon gamma (IFN( ) and they are responsible primarily for cell-mediated immunity such as delayed type hypersensitivity and antiviral immunity. Type 2 (Th2) cells produce interleukins, IL4, IL-5, IL-6, IL-9, IL-10 and IL-13 and are primarily involved in assisting humoral immune responses such as those seen in response to allergens, e.g. IgE and IgG4 antibody isotype switching (Mosmann, 1989, *Annu Rev Immunol*, 7:145–173). D-guanosine analogs have been shown to elicit various effects on lymphokines IL-1, IL-6, IFN∀ and TNF∀ (indirectly) in vitro (Goodman, 1988, *Int J Immunopharmacol*, 10, 579–88) and in vivo (Smee et al., 1991, *Antiviral Res* 15: 229). However, the ability of the D-guanosine analogs such as 7-thio-8-oxoguanosine to modulate Type I or Type 2 cytokines directly in T cells was ineffective or had not been described.

Thus, there remains a need for novel L-nucleoside analogs, including novel purine L-nucleoside analogs. There is a particular need for novel purine L-nucleosides which have immunomodulatory activity, and especially for novel purine L-nucleosides which modulate Th1 and Th2 activity.

BRIEF DESCRIPTION OF THE INVENTION

The present invention is directed to novel purine L-nucleoside compounds, their therapeutic uses and synthesis.

In one aspect of the invention, there are provided purine L-nucleoside analogs of Formulas 1–4.

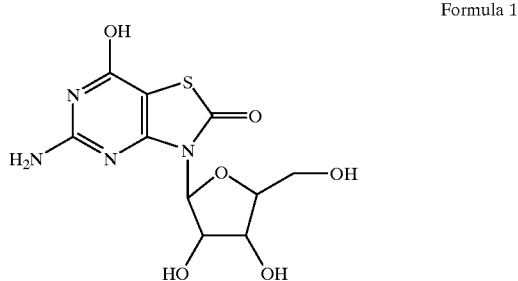

Formula 1

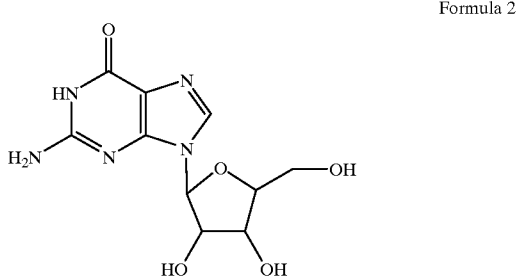

Formula 2

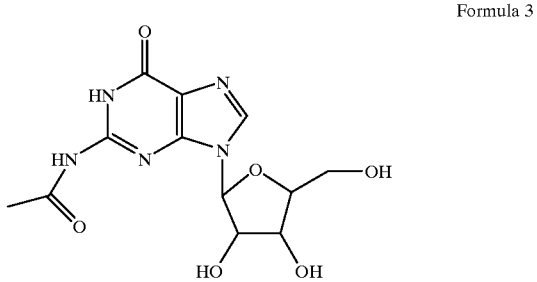

Formula 3

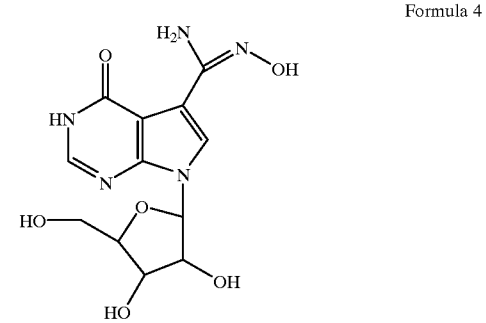

Formula 4

In another aspect of the invention, a pharmaceutical composition comprises a therapeutically effective amount of a compound of Formula 1, 2, 3, or 4, or a pharmaceutically acceptable ester or salt thereof admixed with at least one pharmaceutically acceptable carrier.

In yet another aspect of the invention, a compound according to Formulas 1–4 is used in the treatment of any condition which responds positively to administration of the compound, and according to any formulation and protocol which achieves the positive response. Among other things it is contemplated that compounds of Formulas 1–4 may be used to treat an infection, an infestation, a cancer, tumor or other neoplasm, or an autoimmune disease.

DETAILED DESCRIPTION

Figure 1:
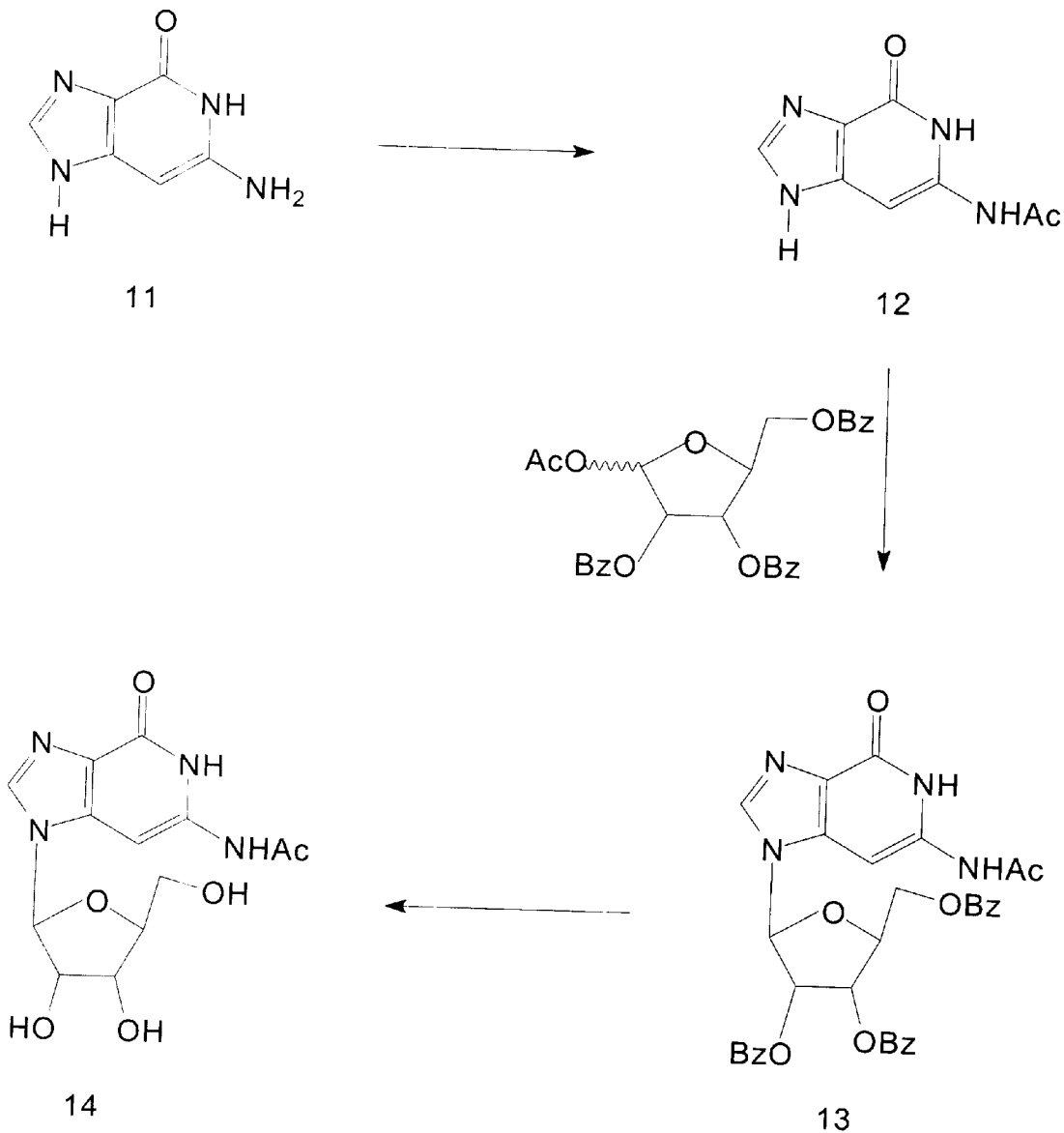
FIGS. 1 and 2 (Schemes 1 and 2) depict synthetic chemical steps which may be used to synthesize the compounds according to the present invention. Schemes pertaining to the synthesis of a particular composition are referenced in the examples set forth herein.
Figure 2:
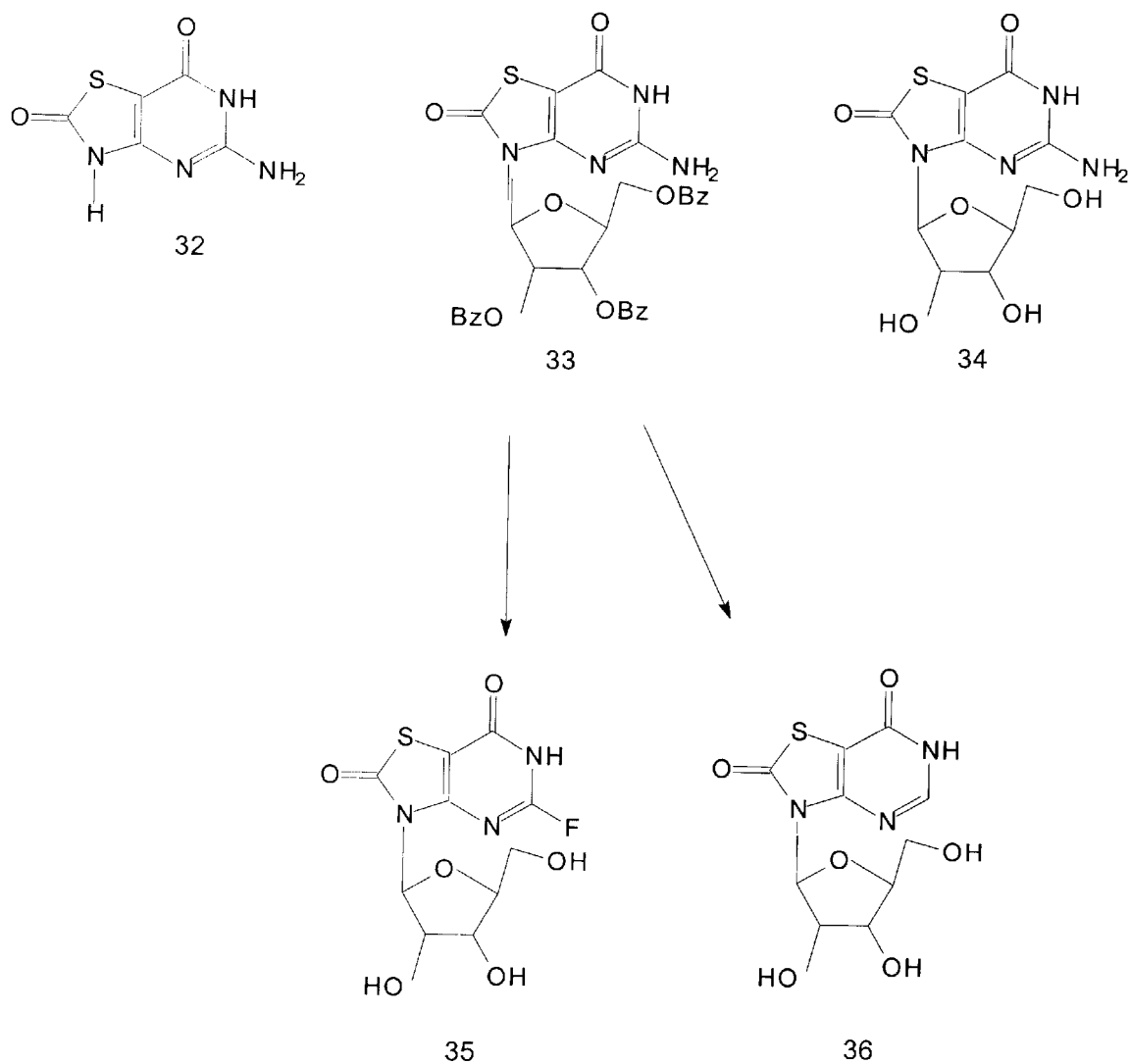

Where the following terms are used in this specification, they are used as defined below.

The term "nucleoside" refers to a compound composed of any pentose or modified pentose moiety attached to a specific position of a heterocycle or to the natural position of a purine (9-position) or pyrimidine (1-position) or to the equivalent position in an analog.

The term "nucleotide" refers to a phosphate ester substituted on the 5'-position of a nucleoside. The term "purine" refers to nitrogenous bicyclic heterocycles. The term "pyrimidine" refers to nitrogenous monocyclic heterocycles.

The term "D-nucleosides" that is used in the present invention describes the nucleoside compounds that have a D-ribose sugar moiety (e.g., Adenosine). The term "L-nucleosides" that is used in the present invention describes the nucleoside compounds that have an L-ribose sugar moiety.

The term "L-configuration" is used throughout the present invention to describe the chemical configuration of the ribofuranosyl moiety of the compounds that is linked to the nucleobases. The L-configuration of the sugar moiety of compounds of the present invention contrasts with the D-configuration of ribose sugar moieties of the naturally occurring nucleosides such as cytidine, adenosine, thymidine, guanosine and uridine.

The term "immunomodulators" refers to natural or synthetic products capable of modifying the normal or aberrant immune system through stimulation or suppression.

The term "effective amount" refers to the amount of a compound of formula (I) which will restore immune function to normal levels, or increase immune function above normal levels in order to eliminate infection.

The compounds of Formulas 1–4 may have multiple asymmetric centers. Accordingly, they may be prepared in either optically active form or as a racemic mixture. The scope of the invention as described and claimed encompasses the individual optical isomers and non-racemic mixtures thereof as well as the racemic forms of the compounds of Formulas 1–4.

The term "α" and "β" indicate the specific stereochemical configuration of a substituent at an asymmetric carbon atom in a chemical structure as drawn. The compounds described herein are all in the L-furanosyl configuration.

The term "enantiomers" refers to a pair of stereoisomers that are non-superimposable mirror images of each other. A mixture of a pair of enantiomers, in a 1:1 ratio, is a "racemic" mixture.

The term "isomers" refers to different compounds that have the same formula. "Stereoisomers" are isomers that differ only in the way the atoms are arranged in space.

"Pharmaceutically acceptable salts" may be any salts derived from inorganic and organic acids or bases.

Compounds

The compounds of the present invention are generally described by Formulas 1–4 having the following structures

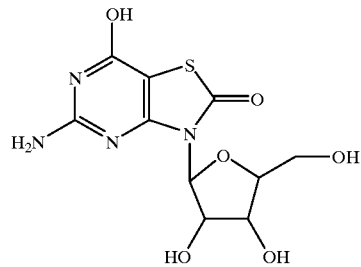

Formula 1

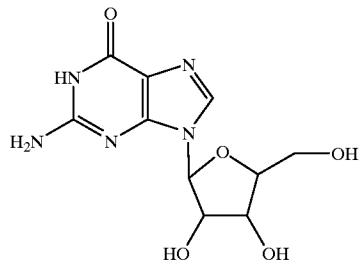

Formula 2

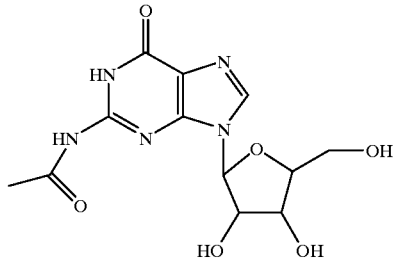

Formula 3

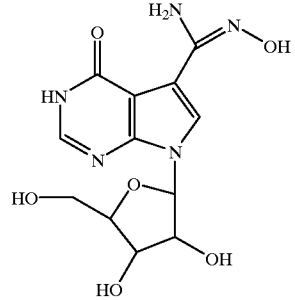

Formula 4

Uses

It is contemplated that compounds according to Formulas 1–4, the compounds of the present invention, will be used to treat a wide variety of conditions, and in fact any condition which responds positively to administration of one or more of the compounds. Among other things it is specifically contemplated that compounds of the invention may be used to treat an infection, an infestation, a cancer or tumor or an autoimmune disease.

Infections contemplated to be treated with the compounds of the present invention include respiratory syncytial virus (RSV), hepatitis B virus (HBV), hepatitis C virus (HCV), herpes simplex type 1 and 2, herpes genitalis, herpes keratitis, herpes encephalitis, herpes zoster, human immunodeficiency virus (HIV), influenza A virus, hantann virus (hemorrhagic fever), human papilloma virus (HPV), measles and fungus.

Infestations contemplated to be treated with the compounds of the present invention include protozoan infestations, as well as helminth and other parasitic infestations.

Cancers or tumors contemplated to be treated include those caused by a virus, and the effect may involve inhibiting the transformation of virus-infected cells to a neoplastic state, inhibiting the spread of viruses from transformed cells to other normal cells and/or arresting the growth of virus-transformed cells.

Autoimmune and other diseases contemplated to be treated include arthritis, psoriasis, bowel disease, juvenile diabetes, lupus, multiple sclerosis, gout and gouty arthritis, rheumatoid arthritis, rejection of transplantation, allergy and asthma.

Still other contemplated uses of the compounds according to the present invention include use as intermediates in the chemical synthesis of other nucleoside or nucleotide analogs which are, in turn, useful as therapeutic agents or for other purposes.

In yet another aspect, a method of treating a mammal comprises administering a therapeutically and/or prophylactically effective amount of a pharmaceutical containing a compound of the present invention. In this aspect the effect may relate to modulation of some portion of the mammal's immune system, especially modulation of lymphokines profiles of Th1 and Th2. Where modulation of Th1 and Th2 lymphokines occurs, it is contemplated that the modulation may include stimulation of both Th1 and Th2, suppression of both Th1 and Th2, stimulation of either Th1 or Th2 and suppression of the other, or a bimodal modulation in which one effect on Th1/Th2 levels (such as generalized suppression) occurs at a low concentration, while another effect (such as stimulation of either Th1 or Th2 and suppression of the other) occurs at a higher concentration.

In general, the most preferred uses according to the present invention are those in which the active compounds are relatively less cytotoxic to the non-target host cells and relatively more active against the target. In this respect, it may also be advantageous that L-nucleosides may have increased stability over D-nucleosides, which could lead to better pharmacokinetics. This result may attain because L-nucleosides may not be recognized by enzymes, and therefore may have longer half-lives.

It is contemplated that compounds according to the present invention will be administered in any appropriate pharmaceutical formulation, and under any appropriate protocol. Thus, administration may take place orally, parenterally (including subcutaneous injections, intravenous, intramuscularly, by intrasternal injection or infusion techniques), by inhalation spray, or rectally, topically and so forth, and in dosage unit formulations containing conventional non-toxic pharmaceutically acceptable carriers, adjuvants and vehicles.

By way of example, it is contemplated that compounds according to the present invention can be formulated in admixture with a pharmaceutically acceptable carrier. For example, the compounds of the present invention can be administered orally as pharmacologically acceptable salts. Because the compounds of the present invention are mostly water soluble, they can be administered intravenously in physiological saline solution (e.g., buffered to a pH of about 7.2 to 7.5). Conventional buffers such as phosphates, bicarbonates or citrates can be used for this purpose. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the ordinary skill of the art to modify the route of administration and dosage regimen of a particular compound in order to manage the pharmacokinetics of the present compounds for maximum beneficial effect in patients.

In certain pharmaceutical dosage forms, the pro-drug form of the compounds, especially including acylated (acetylated or other) derivatives, pyridine esters and various salt forms of the present compounds are preferred. One of ordinary skill in the art will recognize how to readily modify the present compounds to pro-drug forms to facilitate delivery of active compounds to a target site within the host organism or patient. One of ordinary skill in the art will also take advantage of favorable pharmacokinetic parameters of the pro-drug forms, where applicable, in delivering the present compounds to a targeted site within the host organism or patient to maximize the intended effect of the compound.

In addition, compounds according to the present invention may be administered alone or in combination with other agents for the treatment of the above infections or conditions. Combination therapies according to the present invention comprise, the administration of at least one compound of the present invention or a functional derivative thereof and at least one other pharmaceutically active ingredient. The active ingredient(s) and pharmaceutically active agents may be administered separately or together and when administered separately this may occur simultaneously or separately in any order. The amounts of the active ingredient (s) and pharmaceutically active agent(s) and the relative timings of administration will be selected in order to achieve the desired combined therapeutic effect. Preferably the combination therapy involves the administration of one compound of the Present invention or a physiologically functional derivative thereof and one of the agents mentioned herein below.

Examples of such further therapeutic agents include agents that are effective for the modulation of immune system or associated conditions such as AZT, 3TC, 8-substituted guanosine analogs, 2',3'-dideoxynucleosides, interleukin II, interferons such as α-interferon, tucaresol, levamisole, isoprinosine and cyclolignans. Certain compounds according to the present invention may be effective for enhancing the biological activity of certain agents according to the present invention by reducing the metabolism or inactivation of other compounds and as such, are co-administered for this intended effect.

With respect to dosage, one of ordinary skill in the art will recognize that a therapeutically effective amount will vary with the infection or condition to be treated, its severity, the treatment regimen to be employed, the pharmacokinetics of the agent used, as well as the patient (animal or human) treated. Effective dosages may range from 1 mg/kg of body weight, or less, to 25 mg/kg of body weight or more. In general a therapeutically effective amount of the present compound in dosage form usually ranges from slightly less than about 1 mg./kg. to about 25 mg./kg. of the patient, depending upon the compound used, the condition or infection treated and the route of administration. This dosage range generally produces effective blood level concentrations of active compound ranging from about 0.04 to about 100 micrograms/cc of blood in the patient. It is contemplated, however, that an appropriate regimen will be developed by administering a small amount, and then increasing the amount until either the side effects become unduly adverse, or the intended effect is achieved.

Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carrier, such as dextrose, mannitol, lactose and related carriers, diluents, granulating agents, lubricants, binders, disintegrating agents and the like may be used. If desired, the tablets or capsules may be enteric-coated or sustained release by standard techniques.

For parenteral formulations, the carrier will usually comprise sterile water or aqueous sodium chloride solution, though other ingredients including those which aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

Test Results

In vitro tests were performed on a compound according to Formula 1 (5-Amino-3-β-L-ribofuranosylthiazolo[4,5-d]pyrimidine-2,7(6H)-dione) and the results are described below.

Peripheral blood mononuclear cells (PBMCs) were isolated from the buffy coat following Ficoll-Hypaque density gradient centrifugation of 60 ml blood from healthy donors. T-cells were then purified from the PBMCs using Lymphokwik lymphocyte isolation reagent specific for T-cells (LK-25T, One Lambda, Canoga Park Calif.). An average yield of 40–60×10$^6$ T-cells were then incubated overnight at 37° C. in 20–30 ml RPMI-AP5 (RPMI-1640 medium (ICN, Costa Mesa, Calif.) containing 20 mM HEPES buffer, pH 7.4, 5% autologous plasma, 1% L-glutamine, 1% penicillin/streptomycin and 0.05% 2-mercaptoethanol) to remove any contaminating adherent cells. In all experiments, T-cells were washed with RPMI-AP5 and then plated on 96-well microtitre plates at a cell concentration of 1×10$^6$ cells/ml.

The T-cells were activated by the addition of 500 ng ionomycin and 10 ng phorbol 12-myristate 13-acetate (PMA) (Calbiochem, La Jolla, Calif.) and incubated for 48–72 h at 37° C. PMA/ionomycin-activated T-cells were treated with 0.5–50 μM of the compound being tested, or with 250–10000 U/ml of a control antiviral, interferon-alpha (Accurate, Westbury, N.Y.) immediately following activation and re-treated 24 h later. T-cells from each plate were used for immunofluorescence analysis and the supernatants used for extracellular cytokine measurements. Following activation, 900 μl cell supernatant from each microplate was transferred to another microplate for analysis of cell-derived cytokine production. The cells are then used in immunofluorescence analyses for intracellular cytokine levels and cytokine receptor expression.

Cell-derived human cytokine concentrations were determined in cell supernatants from each microplate. Activation-induced changes in interleukin-2 (IL-2) levels were determined using a commercially available ELISA kit (R & D systems Quantikine kit, Minneapolis, Minn.) or by bioassay using the IL-2-dependent cell line, CTLL-2 (ATCC, Rockville, Md.). Activation-induced changes in interleukin-4 (IL-4), tumor necrosis factor (TNFα) interleukin-8 (IL-8) (R & D systems (Quantikine kit, Minneapolis, Minn.) and interferon-gamma (IFN-γ) (Endogen (Cambridge, Mass.) levels were determined using ELISA kits. All ELISA results were expressed as pg/ml and the CTLL-2 bioassay as counts per minute representing the IL-2-dependent cellular incorporation of $^3$H-thymidine (ICN, Costa Mesa, Calif.) by CTLL-2 cells.

Figure 3:
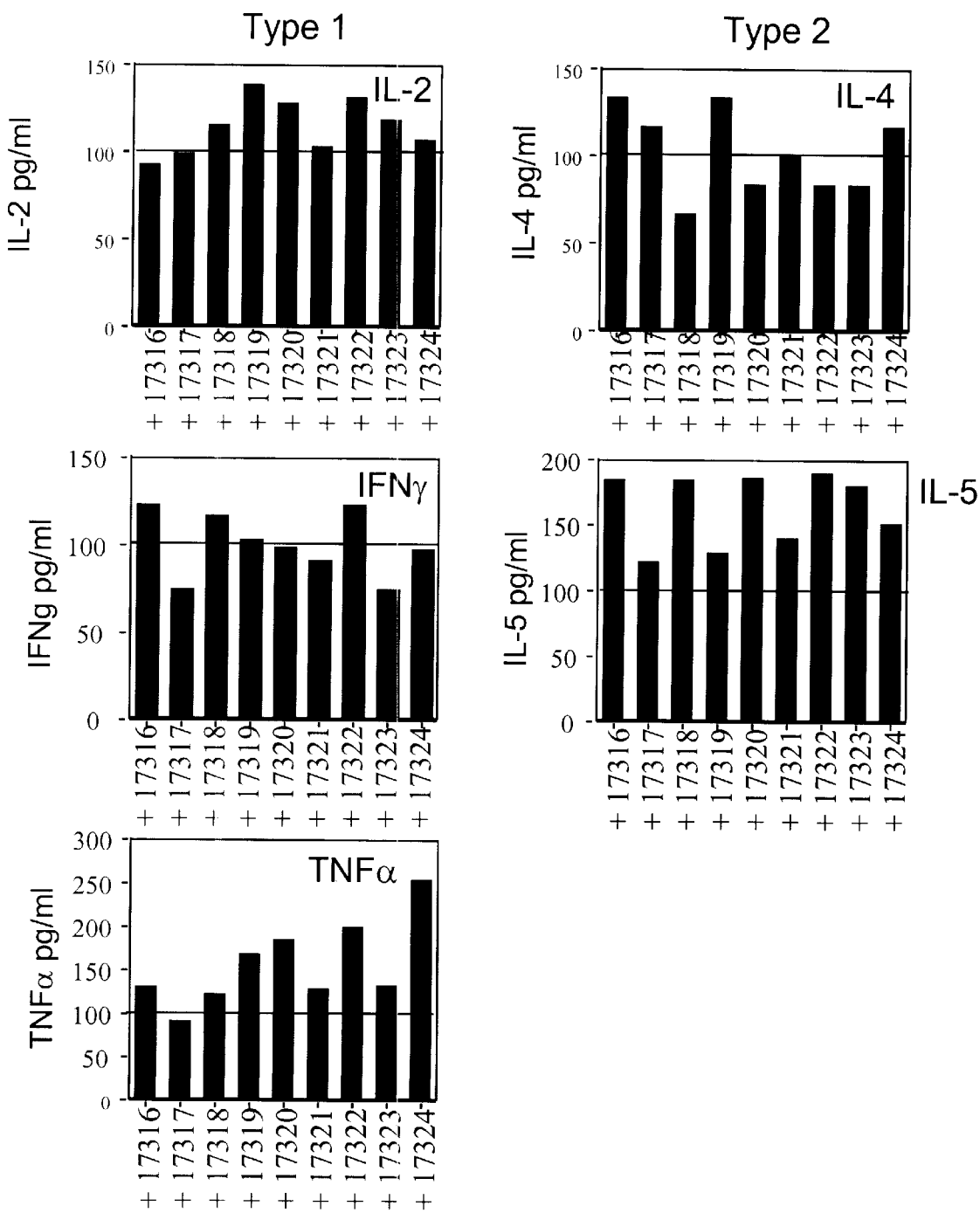
FIG. 3 is a graphical depiction of an exemplary L-guanosine analog on Th1 and Th2.

The results for the compound according to Formula 1 on IL-2 TNFα, IFN-γ, IL-4 and IL-5 levels are presented in FIG. 3 in column +17323.

Synthesis

The compounds of the present invention may be produced according to synthetic methods which are individually readily known to those of ordinary skill in the art. In general, compounds according to the present invention are synthesized by condensing appropriate nucleoside base with the necessary sugar synthon to give the protected L-nucleoside which on further manipulation and deprotection of the sugar hydroxyl protecting groups will ultimately give rise to nucleoside analog having the desired ribofuranosyl moiety of the L-configuration.

Scheme 1 shows the synthesis of N$^2$-acetyl-3-deaza-L-guanosine. 3-Deazaguanine 11 (Cook et al. *J. Med. Chem.* 1976, 27, 1389) was treated with acetic anhydride in pyridine to yield N$^2$-acetyl-3-deazaguanine 12, which was silylated and coupled with 1-acetyl-2,3,5-O-tribenzoyl-L-ribose to give compound 13. Removal of benzoyl group with ammonia-methanol yielded N$^2$-acetyl-3-deaza-L-guanosine 14.

Scheme 2 shows the synthesis of 5-amino-3-β-L-ribofuranosylthiazolo[4,5-d]pyrimidine-2,7(6H)-dione and analogs. 5-Aminothiazolo[4,5-d]pyrimidine-2,7(3H, 6H)-dione 32 (Baker et al. *J. Chem. Soc. C* 1970, 2478) was coupled with the deprotected ribose to give the nucleoside 33, which was deprotected to give 5-amino-3-β-L-ribofuranosylthiazolo[4,5-d]pyrimidine-2,7(6H)-dione 34. Compound 33 can be protected with nitrophenethyl group and then treated with butyl nitrite and hydrogen fluoride in pyridine to give the fluoride derivative 35. Treatment of 33 with t-butyl nitrite (Nagahara et al. *J. Med. Chem.* 1990, 33, 407) in THF can replace the amino group with hydrogen to give 36.

The compounds described in the schemes are β-L-guanosine analogs. The corresponding α-L-analogs can be prepared in a similar manner, but with L-ribose having different protecting groups. 1-Acetyl-2,3,5-O-tribenzoyl-L-ribofuranose can be replaced with 1-bromo-β-L-ribose derivatives as reagent, which would produce α-L-nucleosides as major products.

EXAMPLES

The following section give the experimental samples performed in the applicants' laboratory. The examples try to be broad, but not comprehensive. The work performed includes all the samples described below, but not limited to these examples.

Example 1

$N^2$-Acetyl-3-deazaguanine 12

To a suspension of 3-Deazaguanine 11 (2.0 g) in anhydrous pyridine (30 mL) was added acetic anhydride (5 mL) and the resulting reaction mixture heated to 90° C. Solid was dissolved gradually and a brown solution formed. After 10 minutes the precipitates reoccurred. The mixture was stirred at 90° C. for additional 90 minutes and cooled to 50° C. The precipitates were filtered and washed with acetonitrile, water, and acetonitrile again to give 1.79 g of $N^2$-acetyl-3-deazaguanine 12 as a light-brown solid.

Example 2

$N^2$-Acetyl-3-deaza-β-L-guanosine 14

A suspension of $N^2$-acetyl-3-deazaguanine 12 (576 mg, 3.0 mmol), hexamethyldisilazane (HMDS, 15 mL), pyridine (2 mL), and ammonium sulfate (10 mg) was stirred under reflux and exclusion of moisture for 2.5 h. Solvents were evaporated and the residue dried under vacuum for 2 h to give a foam syrup. The residue was dissolved in methylene chloride (anhydrous, 30 mL) and 1-Acetyl-2,3,5-tribenzoyl-L-robose (1.51 g, 3.0 mmol) added, followed by slow addition of trimethylsilyl triflate (4.5 mmol, 0.81 mL). The resulting solution was refluxed for 20 h. Solvent was evaporated and the residue dissolved in ethyl acetate, washed with 5% NaHCO3, dried (NA2SO4), and concentrated. Chromatography on silica with 5%Et3N and 2–10% ethanol in methylene chloride gave three major products: 340 mg of higher Rf product, 368 mg of the medium Rf product, and 335 mg of the lower Rf product, all as a slightly yellow solid.

A solution of the medium Rf product 13 (350 mg) in saturated ammonia-methanol stood at room temperature for two days. Ammonia and methanol were evaporated and the residue was chromatographed on silica with 5%Et3N and 20% ethanol in methylene chloride to give 114 mg of $N^2$-acetyl-3-deaza-β-L-guanosine as 14 as a white solid.

Example 3

5-Amino-3-β-L-ribofuranosylthiazolo[4,5-d]pyrimidine-2,7(6H)-dione 34

5-Aminothiazolo[4,5-d]pyrimidine-2,7(6H)-dione 32 (400 mg, 2.71 mmol) was suspended in acetonitrile (16 mL) and hexamethyldisilazane (0.96 mL), and trimethylchlorosilane (0.55 mL) and trimethylsilyl triflate (0.9 mL) added. The mixture was stirred under reflux for 3.5 h. A solution of trimethylsilyl triflate (0.45 mL) in acetonitrile (1.0 mL) was added dropwise and stirring and heating was continued for additional 30 min. A slurry of 1-O-acetyl-2,3,5-O-tribenzoyl-L-ribofuranose (1.22 g, 2.28 mmol) in acetonitrile (4.1 mL) was added and the mixture stirred under reflux for 30 min. The reaction mixture was cooled and slowly poured into a vigorously stirred mixture of sodium bicarbonate (2.81 g) and water (96 mL), which produced a stick solid. Ethyl acetate was added, the mixture stirred until the solid dissolved. The aqueous layer was extracted with ethyl acetate twice and the combined organic layer washed with sodium bicarbonate, dried (Na2SO4), and concentrated. The crude was purified by chromatography on silica with 5%Et3N and 5% ethanol in methylene chloride to give 1.10 g of 5-amino-3-(2',3',5'-O-tribenzoyl-β-L-ribofuranosyl)thiazolo[4,5-d]pyrimidine-2,7(6H)-dione 33 as a white solid.

5-Amino-3-(2',3',5'-O-tribenzoyl-β-L-ribofuranosyl)thiazolo[4,5-d]pyrimidine-2,7(6H)-dione 33 (1.09 g, 1.717 mmol) was dissolved in methanol (25 mL) and sodium methoxide (5.4 M in methanol, 0.64 mL) added. The solution stood at room temperature for 64 h. Most methanol was evaporated and water (20 mL) and Amberite H-Form (1.0 g) added. The suspension was stirred gently for 20 min and the resin filtered by suction, washed with water (2×10 mL). The filtrate was concentrated and the crude product was purified by crystallization from methanol to give 368 mg of 5-Amino-3-β-L-ribofuranosylthiazolo[4,5d]pyrimidine-2,7 (6H)-dione 34 as a colorless solid.

We claim:

1. A compound having a structure according to Formula 1:

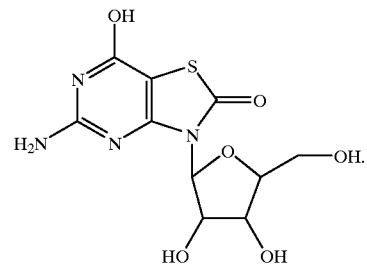

Formula 1

2. A compound having a structure according to Formula 4:

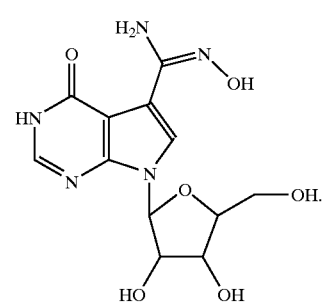

Formula 4

3. A pharmaceutical comprising a compound according to claims 1 or 2, or a pharmaceutically acceptable ester or salt thereof, admixed with at least one pharmaceutically acceptable carrier.

* * * * *